United States Patent [19]

Penco et al.

[11] 4,131,649

[45] Dec. 26, 1978

[54] DAUNORUBICIN DERIVATIVES, THEIR PREPARATION AND THEIR USE

[75] Inventors: Sergio Penco; Francesco Angelucci; Federico Arcamone, all of Milan, Italy

[73] Assignee: Societa Farmaceutici Italia S.p.A., Milan, Italy

[21] Appl. No.: 810,077

[22] Filed: Jun. 27, 1977

[30] Foreign Application Priority Data

Jul. 13, 1976 [GB] United Kingdom ............... 28986/76

[51] Int. Cl.$^2$ ....................... A61K 31/70; C07H 15/24
[52] U.S. Cl. .......................................... 424/180; 536/4; 536/17
[58] Field of Search ....................... 536/17 A; 424/180

[56] References Cited

U.S. PATENT DOCUMENTS 4,020,270   4/1977   Arcamone et al. ............... 536/17 A
4,025,623   5/1977   Arcamone et al. ............... 536/17 A

*Primary Examiner*—Johnnie R. Brown
*Attorney, Agent, or Firm*—Hubbell, Cohen, Stiefel & Gross

[57] ABSTRACT

Daunorubicin (also known as daunomycin) derivatives of the formula

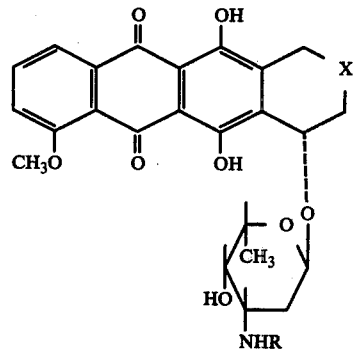

wherein X is

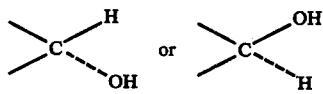

and R is —COCF$_3$ or H which are prepared by hydrogenating 9-desacetyl-9-keto-N-trifluoroacetyl-daunorubicin, an unexpectedly stable key-intermediate which is itself a new compound, are useful in treating certain mammalian tumors.

8 Claims, No Drawings

DAUNORUBICIN DERIVATIVES, THEIR PREPARATION AND THEIR USE

The invention described herein was made in the course of work performed under a grant from the United States Department of Health, Education and Welfare.

CROSS REFERENCE TO RELATED APPLICATIONS

None.

BACKGROUND OF THE INVENTION

Field of the Invention

The invention relates to glycoside antibiotics, their preparation and use.

The Prior Art

The glycoside antibiotics daunorubicin (also known as daunomycin) and doxorubicin (also known as adriamycin) are respectively described and claimed in British Patents 1,003,383 and 1,161,278, both of which are owned by the unrecorded assignee hereof.

SUMMARY OF THE INVENTION

The present invention provides, in one aspect thereof, a new class of daunorubicin derivatives which are useful in treating certain mammalian tumors. These new derivatives are compounds of the formula I

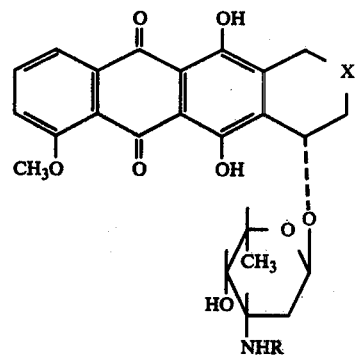

wherein X is

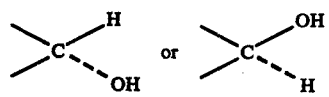

and R is —COCF$_3$ or H

The invention also provides a process of preparing these derivatives. The process proceeds through a novel intermediate, 9-desacetyl-9-keto-N-trifluoroacetyldaunorubicin, which also forms part of the invention. This intermediate is an unexpectedly stable compound, which, when hydrogenated with an alkali metal borohydride leads to the compounds of formula I. According to the process of the invention which is schematically shown below, daunorubicin (II) is converted into 9-desacetyl-9-keto-N-trifluoroacetyldaunorubicin (V).

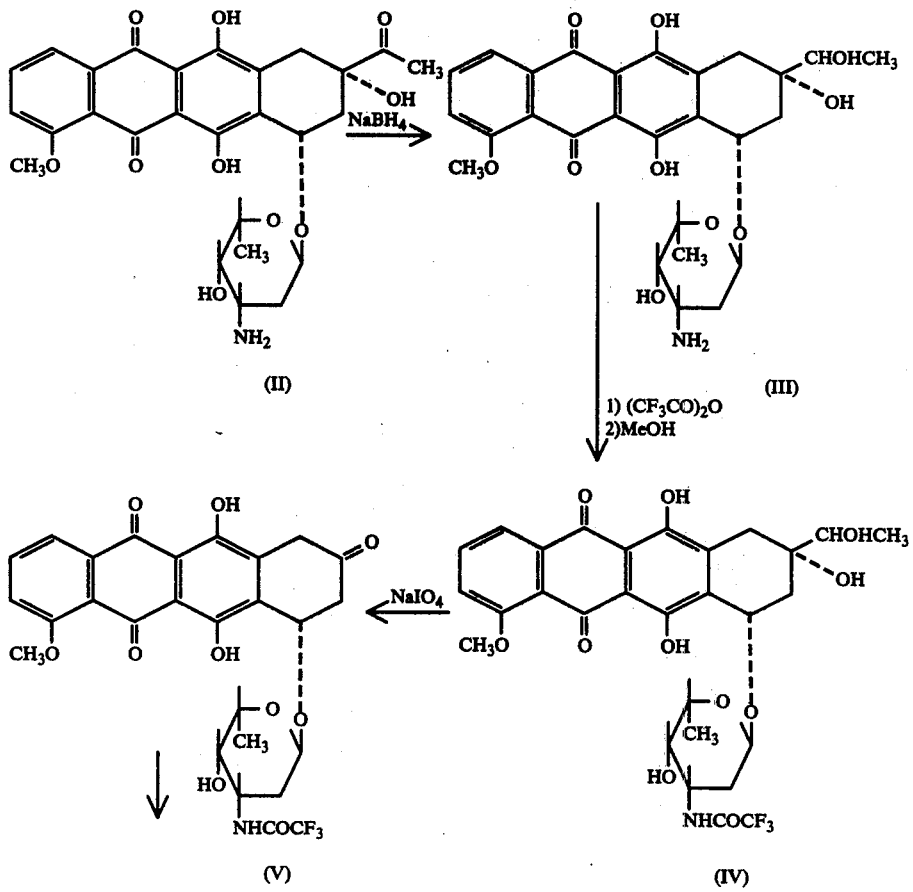

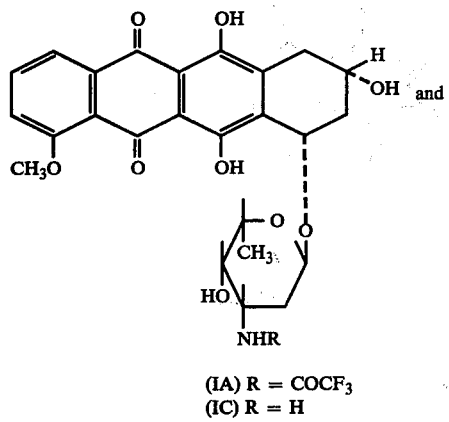
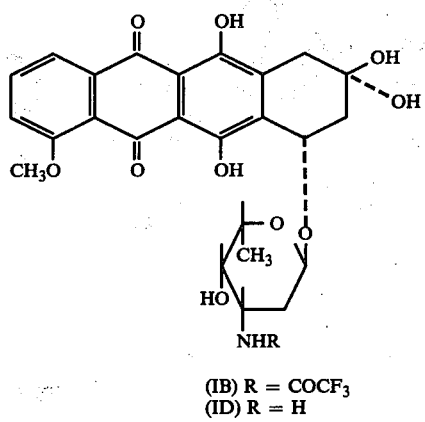

(IA) R = COCF₃
(IC) R = H (IB) R = COCF₃
(ID) R = H

In more detail, as shown above, the carbonyl group at the 13-position of daunorubicin (II) is reduced to the corresponding alcohol (III) with sodium borohydride. The reaction is carried out in water at room temperature to give (III), isolated as the hydrochloride, in about 80% yield. The amino group in the sugar residue of the resulting alcohol (III) is protected with an N-trifluoroacetyl group which is subsequently removed under mild conditions that do not affect the remaining portion of the anthracycline molecule. The N-trifluoroacetylation is performed by treatment with trifluoroacetic anhydride, followed by hydrolysis of the O-trifluoroacetyl group with methanol to form a protected derivative (IV) in 74% yield. The oxidation of (IV) is carried out in t-butyl alcohol in the presence of two equivalents of sodium periodate at room temperature for two hours. The protected intermediate (IV), which is insoluble in the reaction mixture, was obtained in about 50% yield. The compound (IV), by treatment with sodium borohydride-cyanide (NaBH₃CN) under acid conditions, is converted into an epimeric mixture of (IA) and (IB) in an approximate ratio of 8:1. The separation of these compounds by chromatography on a column of silicic acid, followed by mild alkaline treatment to remove the N-trifluoroacetyl protective group, gives 9-desacetyl-daunorubicin (IC) and 9-desacetyl-9-epi-daunorubicin (ID) both isolated as the hydrochlorides.

The new compounds (IC) and (ID) both display anti-mitotic activity and are useful therapeutic agents for the treatment of mammalian tumors.

DESCRIPTION OF THE PREFERRED EMBODIMENTS

The invention will now be illustrated by the following Examples.

EXAMPLE 1

N-trifluoroacetyl-13-dihydrodaunorubicin (IV)

A solution of 3.0 g. of daunorubicin hydrochloride (II) in 300 ml. of water was adjusted to pH 9.5 with aqueous 0.1 N sodium hydroxide and treated with 0.3 g. of sodium borohydride at room temperature for seven minutes. The reaction mixture was poured into 750 ml. of aqueous 0.25 N hydrochloric acid with vigorous stirring to eliminate the excess reducing agent (NaBH₄). The solution was then adjusted to pH 8.6 and extracted with chloroform until the extracts were no longer colored. The chloroform extracts were combined, dried over anhydrous sodium sulphate, and evaporated under vacuum to 50 ml. The resulting red solution, after being adjusted to pH 3.5 (Congo Red) with anhydrous methanolic hydrogen chloride, was mixed with excess diethyl ether to give 2.8 g. of pure 13-dihydrodaunorubicin (III) as the hydrochloride.

A suspension of the 2.8 g. of 13-dihydrodaunorubicin hydrochloride (III) in 300 ml. of chloroform was treated with 20 ml. of trifluoroacetic anhydride at 0° for 1 hour. The reaction mixture was evaporated to a residue under vacuum. The residue was dissolved in 200 ml. of methanol and neutralized with an aqueous saturated solution of sodium bicarbonate. After 30 minutes at room temperature, the solvent was eliminated under vacuum and the aqueous solution was extracted with chloroform until the extracts were no longer colored. The chloroform extracts were combined, washed with water, dried over anhydrous sodium sulphate, evaporated to 30 ml., and then mixed with excess petroleum ether to give 2.3 g. of pure N-trifluoroacetyl-13-dihydrodaunorubicin (IV); m.p. 164°–166° C. (dec.); TLC (Thin Layer Chromatography) on Merck Kieselgel 60 F₂₅₄ using a chloroform-acetone solvent system (2:1 v/v) = Rf 0.25.

EXAMPLE 2

9-Desacetyl-9-keto-N-trifluoroacetyldaunorubicin (V)

A solution of 2.4 g. of N-trifluoroacetyl-13-dihydrodaunorubicin (IV) in 120 ml. of t-butyl alcohol was treated with 1.6 g. of sodium periodate dissolved in 120 ml. of water. The reaction mixture was stirred at room temperature for two hours. The resulting precipitate (V) was filtered off, washed with water and dried under vacuum to yield 1.4 g. of pure 9-desacetyl-9-keto-N-trifluoroacetyldaunorubicin (V) were obtained; m.p. 200° C. (dec.); TLC on Merck Kieselgel 60 F₂₅₄ using a chloroform-acetone solvent system (2:1 v/v) = Rf 0.57.

| Elemental analysis: | calcd. % for $C_{27}H_{24}F_3NO_{10}$: | H 4.18; C 55.9 |
|---|---|---|
| | found %: | H 4.26; C 55.6 |

EXAMPLE 3

9-Desacetyl-daunorubicin (IC) and 9-desacetyl-9-epi-daunorubicin (ID)

A solution of 1.7 g. of 9-desacetyl-9-keto-N-trifluoroacetyldaunorubicin (V) in 250 ml. of dioxane and 50 ml. of water was adjusted to pH 3 with aqueous 1 N hydrochloric acid and treated with 1 g. of sodium borohydride cyanide (NaBH$_3$CN) at room temperature for 24 hours, the acid condition being maintained by the addition of 1 N hydrochloric acid. The reaction mixture was mixed with water (300 ml.) and extracted with chloroform (5 × 200 ml.). The organic phase (combined CHCl$_3$ extracts) was washed with water, dried over anhydrous sodium sulphate, and evaporated to a residue under vacuum. The residue (1 g.), containing N-trifluoroacetyl-9-desacetyldaunorubicin (IA) and N-trifluoroacetyl-9-desacetyl-9-epi-daunorubicin (IB) was chromatographed on a column of silica gel using chloroform with increasing amounts of acetone as the eluent to give 0.85 g. of pure N-trifluoroacetyl-9-desacetyldaunorubicin (IA); m.p. 204°–206° C. (dec.); TLC on Merck Kieselgel 60 F$_{254}$ using a chloroform-acetone solvent system (2:1 v/v) = Rf : 0.44 and 0.1 g. of pure N-trifluoroacetyl-9-desacetyl-9-epi-daunorubicin (IB); m.p. 108°–182° C. (dec.); Rf : 0.3 using the same solvent system. In order to hydrolyze off the N-trifluoroacetyl groups, the products were treated as follows: 50 ml. of 0.1 N sodium hydroxide were added, after 30 minutes at 0° C.; the pH was adjusted to 8.4 with 0.1 N hydrochloric acid and the solution was repeatedly extracted with chloroform. The combined chloroform extracts were dried over anhydrous sodium sulphate and evaporated under vacuum to 20 ml. volume. The concentrated solution, upon addition of the stoichiometric amount of methanolic hydrogen chloride and diethyl ether, gave a red precipitate which was collected, washed with diethyl ether and dried under vacuum. 9-Desacetyldaunorubicin (IC) had a m.p. of 166°–167° C. (dec.); [α]$_D^{25}$ = + 282° (c = 0.15 in methanol); TLC on Kieselgel plates F$_{254}$ (Merck) with a chloroform:methanol:water solvent system (13:6:1 v/v) = Rf 0.55.

| | Elemental Analysis: |
|---|---|
| calcd. % for C$_{25}$H$_{27}$NO$_9$HCl: | H 5.42; C 57.52; N 2.68 |
| found: | H 5.45; C 57.16; N 2.42 |

9-Desacetyl-9-epi-daunorubicin (ID) had a m.p. of 176° C. (dec.); Rf = 0.4 using the same solvent system.

BIOLOGICAL ACTIVITY

Table 1

The activity of doxorubicin (also known as adriamycin), 9-desacetyldaunorubicin (IC) and 9-desacetyl-9-epi-daunorubicin (ID) were tested against P 388 lymphocytic leukemia in C.D.F. male mice (tumor inoculum 10$^6$ cells; i.p.). Treatment with drug: i.p. on days 1 to 9.

| Compound | Dose mg/kg | T/C[a] |
|---|---|---|
| Doxorubicin | 4 | 83 |
| | 2 | 180 |
| | 1 | 171 |
| | 0.5 | 142 |
| | 0.25 | 152 |
| 9-desacetyldaunorubicin (IC) | 25 | 73 |
| | 12.5 | 228 |
| | 6.25 | 180 |
| | 3.13 | 174 |
| | 1.56 | 155 |
| 9-desacetyl-9-epi-daunorubicin (ID) | 25 | 66 |
| | 12.5 | 66 |
| | 6.25 | 171 |
| | 3.13 | 157 |
| | 1.56 | 142 |
| daunorubicin | 4 | 88 |
| | 2 | 126 |
| | 1 | 171 |
| | 0.5 | 150 |
| | 0.2 | 155 |

[a] Median survival time expressed as percent of untreated controls.

Table 2

The activity of doxorubicin and 9-desacetyldaunorubicin (IC) were tested against P 388 lymphocytic leukemia in CDF$_1$ male mice (tumor inoculum 10$^6$ cells; i.p.). Treatment with drug:i.p. on days 5, 9 and 13.

| Compound | Dose mg/kg | T/C[a] |
|---|---|---|
| Doxorubicin | 16 | 120 |
| | 8 | 163 |
| | 4 | 136 |
| | 2 | 125 |
| | 1 | 125 |
| Daunorubicin | 16 | 127 |
| | 8 | 111 |
| | 4 | 103 |
| | 2 | 107 |
| | 1 | 98 |
| 9-desacetyldaunorubicin (IC) | 113 | 116 |
| | 75 | 181 |
| | 37.5 | 136 |
| | 18.8 | 145 |
| | 9.4 | 133 |
| | 4.7 | 109 |

[a] Median survival time expressed as percent of untreated controls.

The data in Tables 1 and 2 show that the compounds of the invention are considerably more effective and less toxic than doxorubicin.

Modifications and variations can, of course, be made without departing from the spirit and scope of the invention.

Having thus described our invention what we desire to secure by Letters Patent and hereby claim is:

1. A compound of the formula I:

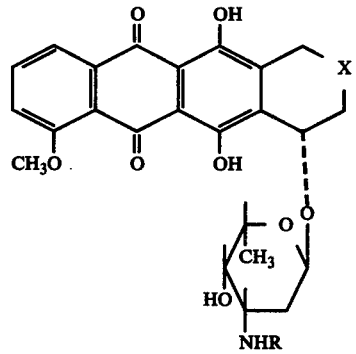

wherein X is

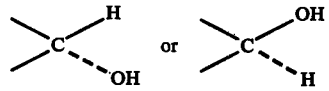

and R is —COCF$_3$ or H.

2. A compound according to claim 1, which is N-trifluoroacetyl-9-desacetyldaunorubicin.

3. A compound according to claim 1, which is N-trifluoroacetyl-9-desacetyl-9-epi-daunorubicin.

4. A compound according to claim 1, which is 9-desacetyldaunorubicin.

5. A compound according to claim 1, which is 9-desacetyl-9-epi-daunorubicin.

6. 9-Desacetyl-9-keto-N-trifluoroacetyl-daunorubicin.

7. A process for the preparation of a compound according to claim 1, which comprises oxidizing N-trifluoroacetyl-13-dihydrodaunorubicin in t-butyl alcohol in the presence of two equivalents of sodium periodate at room temperature for two hours to obtain 9-desacetyl-9-keto-N-trifluoroacetyldaunorubicin, treating same with sodium borohydride-cyanide under acidic conditions at room temperature for 24 hours to form an epimeric mixture of the N-trifluoroacetyl derivatives of 9-desacetyldaunorubicin and 9-desacetyl-9-epi-daunorubicin, separating the epimeric compounds by silica gel chromatography using chloroform with increasing amount of acetone as the eluent, treating the thus separated epimeric compounds with 0.1 N sodium hydroxide at 0° C. for 30 minutes, to hydrolyze off the N-trifluoroacetyl groups and obtain the compounds of formula I, wherein R is hydrogen.

8. A method of inhibiting the growth of P 388 lymphocytic leukemia which comprises intraperitoneally administering to a host afflicted therewith, a compound according to claim 1, wherein R is hydrogen in an amount sufficient to inhibit the growth thereof.

* * * * *

UNITED STATES PATENT OFFICE
CERTIFICATE OF CORRECTION

Patent No. 4,131,649    Dated December 26, 1978

Inventor(s) Sergio Penco et al

It is certified that error appears in the above-identified patent and that said Letters Patent are hereby corrected as shown below:

Column 4, line 40: "(Thim" should read -- (Thin --.

*Signed and Sealed this*

Seventeenth *Day of* July 1979

[SEAL]

Attest:

Attesting Officer

LUTRELLE F. PARKER
*Acting Commissioner of Patents and Trademarks*